United States Patent
Konishi et al.

(10) Patent No.: US 6,932,990 B2
(45) Date of Patent: Aug. 23, 2005

(54) CARBOHYDRATE ABSORPTION INHIBITOR AND METHOD FOR MANUFACTURING THE SAME

(75) Inventors: Yotaro Konishi, Osaka (JP); Michio Aitani, Hyogo (JP); Hiroshi Yamaguchi, Aichi (JP); Tsutomi Arimuba, Osaka (JP); Tadashi Okada, Aichi (JP); Hiromichi Murai, Aichi (JP)

(73) Assignee: Oryza Oil & Fat Chemical Co., Ltd., Aichi (JP)

( * ) Notice: Subject to any disclaimer, the term of this patent is extended or adjusted under 35 U.S.C. 154(b) by 20 days.

(21) Appl. No.: 10/343,488

(22) PCT Filed: Jul. 26, 2001

(86) PCT No.: PCT/JP01/06436
§ 371 (c)(1),
(2), (4) Date: Jan. 31, 2003

(87) PCT Pub. No.: WO02/09734
PCT Pub. Date: Feb. 7, 2002

(65) Prior Publication Data
US 2003/0161903 A1  Aug. 28, 2003

(30) Foreign Application Priority Data
Aug. 1, 2000  (JP) ........................................ 2000-232930

(51) Int. Cl.$^7$ ................................................ A61K 35/78
(52) U.S. Cl. ........................................ 424/776; 424/725
(58) Field of Search .................................. 424/725, 776

(56) References Cited

FOREIGN PATENT DOCUMENTS

| EP | 423419 | 4/1991 |
|---|---|---|
| JP | 9-176019 | 7/1997 |
| WO | WO97/023210 | 7/1997 |
| WO | WO 00/18416 A1 * | 4/2000 |

OTHER PUBLICATIONS

Shahidi et al. (J. Food Lipids (1997), vol. 4, pp. 75–86).*
Wettasinghe et al. (J. Agric. Food Chem. (1999), vol. 47, pp. 1801–1812).*
Quesada, Christina et al., "Phenoloc inhibitors of alpha–amylaseand trypsin enzymes by extracts from pears, lentils, and cocoa", J. Food Protection, (1996), vol. 59, No. 2, pp. 185 to 192.
Honda, Miwa et al., "Inhibition of rat small intestinal sucrase and alpha–glucosidase activities by tea polyphenols", Bioscience Biotechnology and Biochemistry, (1993), vol. 57, No. 1, pp. 123 to 124.
Cannell, Richard J.P., "Purification and characterization of pentagalloylglucose, an a–glucosidase inhibitor/antibiotic from the freshwater greean alga *Sprogyra varians*", Biochem. J., vol. 255, No. 3, pp. 937 to 941.
Araki Hiroko et al., "Effects of Polyphenols on the activities of salivary and pancreatic a–Amylases", Kiyo–Seitoku Eiyo Tanki Daigaku, (1994), vol. 25, pp. 15 to 20.
Lu, Fei et al., "Phenolic antioxidant components of evening primrose", Chemical Abstracts (1996), vol. 124, No. 23, pp. 694, abstract no. 124:312296.
Zinsmeister, Hans D. et al., "Tannin studies of the genus Oenothera", Chemical Abstracts (1970), vol. 73, p. 58, abstract no. 63208.

* cited by examiner

*Primary Examiner*—Susan D. Coe
(74) *Attorney, Agent, or Firm*—Clark & Brody (57) ABSTRACT

This invention provides carbohydrate absorption inhibitor derived from evening primrose seed which is significantly effective to prevent and cure diabetes mellitus and prevent obesity, and the manufacturing method of the same.

Carbohydrate absorption inhibitor in this invention is characterized that the effective component is an alcohol extract of evening primrose seed. The aforementioned evening primrose seed is preferably a defatted evening primrose seed. Extracting solvent of the aforementioned evening primrose seed is preferably ethanol, or preferably a 70 to 85% (v/v) aqueous ethanol. Also, this invention is characterized that the carbohydrate absorption inhibitor is an effective component of polyphenol derived from evening primrose seed. The polyphenol is preferably one or more substances selected from among gallic acid, ellagic acid, catechin, pentagalloylglucose, procyanidin, and proantocyanidin. The manufacturing method of the carbohydrate absorption inhibitor in this invention is characterized to be composed of the following processes A to C. Process A: evening primrose is compressed, oil is separated then the compressed cake is obtained. Process B: The aforementioned compressed cake is defatted in fat-soluble organic solvent, and defatted substance is obtained. Process C: The aforementioned defatted substance is extracted by alcohol, and then this extracted liquid is concentrated or evaporated.

7 Claims, 5 Drawing Sheets

Suppressive effect on the elevation of blood glucose level of health nondiabetic subjects In the food loading test for 9 normal men and 7 women, the rise in blood glucose level of those in 30 minutes after taking evening primrose was significantly inhibited compared with that of those in a control group.

Fig. 5

CARBOHYDRATE ABSORPTION INHIBITOR AND METHOD FOR MANUFACTURING THE SAME

FIELD OF THE INVENTION

This invention relates to carbohydrate absorption inhibitor and method for manufacturing the same effective against e.g. diabetes prevention, diet, and so forth.

BACKGROUND OF THE INVENTION

Polysaccharide (starch, glycogen or the like) contained in food is hydrolyzed by α-amylase in saliva and pancreas and converted into oligosaccharide such as maltose, isomaltose or the like, then decomposed to glucose by disaccharide degrading enzyme such as α-glucosidase or the like in the small intestine and absorbed.

Thus, α-amylase and α-glucosidase perform an important role as a digestive enzyme for carbohydrate in the body. These enzyme activities affect the blood glucose level. Therefore, it is important to control these enzyme activities for the preventions and medical treatments of diabetes mellitus and obesity.

There are two different types of diabetes mellitus. One is insulin-dependent diabetes mellitus (Type I diabetes) and the other is non-insulin dependent diabetes mellitus (Type II diabetes), and the latter type accounts for more than 90% in the incidence of diabetes mellitus.

The latter type (Type II diabetes) is caused by derangement of carbohydrate and fat metabolism arising from an insufficient insulin action (for instance, insulin-hyposensitivity in the organ, insulin-hyposecretion in pancreas or the like) due to overeating.

Non-insulin dependent diabetes mellitus (Type II diabetes) should be basically controlled by diet therapy or exercise therapy rather than medication. However, such self-control does not always correct the aforementioned metabolic derangement, and medication is very much counted on.

However, it is necessary to consider side effects, dosage and usage of the medicine. In general, medicine is usually an intermixture of various components. Therefore, it is necessary to consider the side effect each component has and adverse effect caused by a prolonged dosage of each component.

Extract from gymnema leaf, guava leaf, banaba leaf, mulberry leaf or the like is widely known as a plant-derived extract which is effective to correct the derangement of carbohydrate metabolism. From the viewpoint of safety, these plant-derived extracts are easily applied to food, drugs and medicines, or the like, therefore effective components or the like of the said plant-derived extracts are now being extensively researched.

Against this background, the inventors in this invention have been investigating contents of polyphenol, SOD-like activities or the like in regard to the various plant-derived extracts, then finally came to focus on ethanol extract of evening primrose seed.

After each of the aforementioned experiments has been conducted, they came to know the fact that this extract contains various polyphenol effective to inhibit the carbohydrate absorption.

This invention aims at providing inhibitor of carbohydrate absorption derived from evening primrose seed and method for manufacturing the said inhibitor of carbohydrate absorption which are significantly effective to prevent or relieve symptoms of diabetes mellitus and to prevent obesity.

SUMMARY OF THE INVENTION

Carbohydrate absorption inhibitor which is the subject matter in this invention is characterized by comprising an effective component of solvent extract of compressed cake derived from the defatted evening primrose, and wherein the said effective component contains polyphenol such as ellagic acid, gallic acid, pentagalloylglucose.

Carbohydrate absorption inhibitor in this invention is characterized in that extracting solvent of the compressed cake derived from the aforementioned evening primrose seed is aqueous ethanol (water/ethanol=15 to 30/70 to 85% (v/v)).

Carbohydrate absorption inhibitor in this invention is characterized in that defatting process is proceeded by using fat-soluble organic solvent.

Chemicals in this invention are characterized in that the aforementioned carbohydrate absorption inhibitor is contained.

Food and drink in this invention are characterized in that the aforementioned carbohydrate absorption inhibitor is contained.

According to the experiment conducted by the inventors, the existing plant-derived extracts (guava, banaba and mulberry) have a strong inhibitory action against amylase, however the enzyme inhibitory activity against amylase is not sufficient.

On the contrary, extract (polyphenol) derived from evening primrose as disclosed in this invention indicates strong enzyme inhibition activities against amylase and glucosidase. Especially the ethanol extract derived from the defatted evening primrose seed comprises a strong inhibitory action and consistent safety. Therefore it is appropriate to mix it with medicine to prevent diabetes mellitus or to diet Evening primrose is an annual grass, biennial grass or herbaceous perennial of oenothera genus. In rare cases, stem of evening primrose may be lignified and grow on bush. The followings are four representative examples.

① *Oenothera laciniata*
② *Oenothera striata*
③ *Oenothera biennis*
④ *Oenothera erythrosepala*

In this invention, species of evening primrose are not limited. Any species can be used.

Oil obtained from evening primrose seed is widely known. The evening primrose oil contains a large amount of γ-linolenic acid and is said to be effective against obesity, diabetes mellitus, hypercholesterolemia, alcohol dependence, aging, and disease caused by insufficient vitamin $B_6$.

Also it is widely known that evening primrose oil is effective to inhibit the action in which linolic acid is converted into γ-linolenic acid when virus infection is experienced, as well as to provide a medical treatment for asthma and atopic disease.

In regard to the fat-soluble component of evening primrose seed, physiological activity is now being researched, however, there is no report about the physiological activity of other substance than fat-soluble component.

Some part of the compressed cake exhausted in the manufacturing process of evening primrose seed is used as an animal feeding staff, or is disposed of as an industrial waste.

In this invention, a new usage of other components than the fat-soluble component of the evening primrose seed can be provided, and at the same time the effective component can be extracted from the compressed cake after taking out the evening primrose oil. It is significant to extract the high value-added effective component from the compressed cake and efficiently recycle the natural resources.

To efficiently extract the effective component (polyphenol) for the carbohydrate absorption inhibition, alcohol is used as an extracting solvent for the aforementioned evening primrose seed. Ethanol is especially recommended. If ehanol is used, effective component (polyphenol) is efficiently extracted and can be used both for external application and food. According to other usages available, methanol, butanol or the like can be used.

The concentration of ethanol as an extracting solvent is preferably 70 to 85% (v/v). If the concentration of ethanol is less than 70% (v/V), polyphenol is not sufficiently extracted. And if the concentration exceeds 85% (v/v), seed oil easily dissolves into the extracting solvent.

Also, alcohol extraction should be repeated preferably at different levels of concentration since the content ratio of polyphenol is improved.

Furthermore, it is preferable to use the defatted evening primrose seed for alcohol extraction since polyphenol is concentrated in the defatted matter by removing oil from the seed. For instance, it is preferable to separate the oil from the evening primrose seed by compressing the said seed, and then to extract and separate the remaining oil of the compressed matter by fat-soluble organic solvent.

It is preferable to use hexane as a fat-soluble organic solvent for defatting since the extracted oil can be used for edible oil and also extract of defatted evening primrose seed can be used for foodstuff or the like. If the extract is used for other objectives than food, other non-polar solvent than hexane can be also used.

The aforementioned polyphenol derived from the evening primrose seed can be extracted preferably by solvent such as ethanol, aqueous ethanol, water or the like. According to the research by inventors, the extract contains gallic acid, ellagic acid, catechin, pentagalloylglucose.

Medicine described in this invention is suitable for the prevention of diabetes mellitus, i.e. the prevention or treatment of non-insulin dependent diabetes mellitus (Type II diabetes), or can be also used for the effective component of antiobesity drugs. For instance, medicine in this invention can be orally administered in any shape of soft and/or hard capsule, tablet, granule, fine granule, or powder medicine. On the other hand, the medicine in this invention can be administered by injection into body tissue, dermis, subdermal muscle or vein, Given dose varies depending on the mode of administration, condition of the disease, age of the patient, or the like. Adults can take the effective component of 0.5 to 5,000 mg per day and children can take 0.5 to 3,000 mg per day.

Concentration of polyphenol component can be varied according to various types of medicine. However, when the medicine is used by oral administration or mucomembranous absorption, the given dose should be 0.01 to 15.0 wt %. When the medicine is used by non-oral administration, the given dose should be 0.01 to 10 wt. The dose mentioned above is only an example and can be varied according to various situations.

This invention suggests various embodiments of ordinary food and drink including snack food (such as chewing gums, candies, caramel candies (taffies), chocolates, cookies, jellies, gummy candies, other tablet shaped candies, or the like), noodles (such as Japanese buckwheat noodles called "Soba", Japanese wheat noodles called "Udon", Chinese noodle or the like), dairy products (such as milk, ice cream, yogurt or the like), seasoning (such as fermented soybean paste called "Miso", soy sauce, or the like), soups and drinks (such as juice, soft drinks including carbonated drinks, coffee, black tea, green tea, isotonic drinks, or the like), of healthy food (such as food in supplement in tablet, capsule or the like), nutraceutical supplement (such as nutrition supplement drinks or the like). Extract (polyphenol) derived from evening primrose seed is accordingly applied to those above or convenience food. For example, ethanol extract of evening primrose seed mixed with powdered cellulose can be spray-dried or freeze-dried and converted into powder, granule, tablet, solution or the like, and then applied to various food and drink.

BRIEF DESCRIPTION OF THE DRAWINGS

(Additional part)

(End of the Additional Part)

DESCRIPTION OF THE PREFERRED EMBODIMENTS

Embodiments of this invention are as follows.
(Manufacture of the Carbohydrate Absorption Inhibitor)
Material: Compressed cake obtained in the manufacturing process of evening primrose oil is used.

Firstly, the compressed cake was crushed, refluxed by hexane, and then the defatted substance was obtained by removing the remaining oil from the said compressed cake. Secondly, the said defatted substance was fluxed in 70% (v/v) aqueous ethanol, and then the said ethanol extract was evaporated until carbohydrate absorption inhibitor (Embodiment 1) was obtained.
(Inhibitory Activity Against α-amylase)

Inhibitory activity (5) of α-amylase in regard to the Embodiment 1 (extract of evening primrose seed) was determined by using an amylase activity measuring kit ("Amylase Test Wako" manufactured by Wako Pure Chemical Industries, Ltd., Japan), which is commercially available. Measuring method using human saliva-derived α-amylase is as follows.

After incubating a mixture of the human saliva-derived α-amylase solution (0.02 mL) and sample solution (0.01 mL) at 37° C. for 5 min., substrate buffer solution (11.0 mL) was added to the said mixture and incubated at 37° C. for 60 min. Then the said mixture was incubated in the boiling water for 5 min., and after the reaction stopped, coloring reagent (11.0 mL) was added and then the absorbance (660 nm) was measured.

After calculating the enzyme activity (%) based on this measured value, the inhibitory activity (5) was calculated by the following formula. The enzyme activity was calculated based on the absorbance (100%) measured under condition where no sample coexisted.

Inhibitory activity (%)=100−enzyme activity (%)

Inhibitory activities (%) in regard to other plant-derived extracts of guava leaf (Comparison 1), banaba leaf (Comparison 2) and mulberry leaf (Comparison 3) were also calculated by the same method as shown in the following chart 1.

CHART 1

| Classification | Extract | Concentration (mg/ml) | Inhibitory activity (%) |
|---|---|---|---|
| Embodiment 1 | Evening primrose seed | 1.0 | 100 |
| Comparison 1 | Guava leaf | 1.0 | 0 |
| Comparison 2 | Banaba leaf | 1.0 | 80 |
| Comparison 3 | Mulberry leaf | 1.0 | 0 |

As described in the above chart 1, it is clear that α-amylase inhibitory activity against the embodiment 1 is higher than any of the others.

Also, after measuring the enzyme activity to the variation of concentration regarding the embodiment 1 (evening primrose seed extract) by using the same method, $IC_{50}$ (50% inhibition concentration) against the α-amylase (derived from human saliva) was found to be 0.5 mg/mL.

In connection with the embodiment 1 (evening primrose seed extract), gallic acid, ellagic acid, catechin, and pentagalloylglucose, $IC_{50}$ (50% inhibition concentration) against the α-amylase derived from pancreas of pig was identified by the same method. The following chart shows the excellent inhibitory activities.

| Chemical compound | $IC_{50}$ (mg/ml) |
|---|---|
| Embodiment 1 (evening primrose seed extract) | 0.01 |
| Gallic acid | 0.4 |
| Ellagic acid | >1.0 |
| Catechin | 0.8 |
| Pentagalloylglucose | 0.02 |
| [α-glucosidase inhibitory activity] | |

Next, α-glucosidase inhibitory activity (%) in regard to the embodiment 1 (evening primrose seed extract) was identified by the following method. As for the α-glucosidase for this measurement, 0.1 mol maleic acid buffer solution (pH 6.0) was added to the acetone powder in the intestinal canal of rat (SIGMA CHEMICAL CO.) and homogenized in ice by using a glass homogenizer, and then centrifugalized supernatant was diluted 20 times. Measuring method is shown below.

Sample solution (0.01 ml) was added to the enzyme solution (0.05 ml), then 0.1 M maleic buffer solution (0.64 ml), moreover, 33 mM 4-methylumbelliferyl-α-D-glucoside (0.3 ml) was added and then incubated at 37° C. for 30 min.

After that, the reaction was suspended by adding 3 ml glycin buffer solution (pH 10.3) and the quantity of the isolated 4-methylumbelliferyl was determined by using a fluorometer (excitation wavelength: 366 nm & fluorescent wavelength: 450 mm). Enzyme activity was calculated based on this determined value and inhibitory activity (%) was calculated by the following formula. Also, the enzyme activity was calculated based on the determined value (100%) of 4-methylumbelliferyl measured under condition where no sample coexisted.

Inhibitory activity (%)=100−Enzyme activity (%)

As a comparison, the inhibitory activities (%) in regard to the plant-derived extracts—guava leaf extract (Comparison 1), banaba leaf extract (Comparison 2), and mulberry leaf (Comparison 3) were identified by the same method. Result is shown in the following chart 2.

CHART 2

| Classification | Extract | Concentration (mg/ml) | Inhibitory activity (%) |
|---|---|---|---|
| Embodiment 1 | Evening primrose seed | 0.1 | 65 |
| Comparison 1 | Guava leaf | 0.1 | 77 |
| Comparison 2 | Banaba leaf | 0.1 | 76 |
| Comparison 3 | Mulberry leaf | 0.1 | 96 |

As indicated in Chart 2, although inhibitory activity against α-glucosidase of embodiment 1 (evening primrose seed extract) is less effective than that of guava leaf extract (Comparison 1), banaba leaf extract (Comparison 2) and mulberry leaf extract (Comparison 3), it still has excellent inhibitory activity against α-glucosidase.

After measuring the enzyme activities to the variation of concentration in regard to the embodiment 1 (evening primrose seed extract), gallic acid, ellagic acid, catechin and penthagalloylglucose by using the same method, $IC_{50}$ (50% inhibitory concentration) against α-glucosidase was identified.

The following chart shows the excellent inhibitory activities.

| Chemical compound | $IC_{50}$ (mg/ml) |
|---|---|
| Embodiment 1 (evening primrose seed extract) | 0.1 |
| Gallic acid | 0.8 |
| Ellagic acid | >0.08 |
| Catechin | 0.8 |
| Pentagalloylglucose | 0.04 |

Those test results indicate that the embodiment 1 (evening primrose seed extract) comprises the inhibitory activity against both α-amylase and α-glucosidase, and effectively inhibits the degradation of carbohydrate.

(Carbohydrate Loading Test to Normal Rats)

In regard to the embodiment 1 (evening primrose seed extract), carbohydrate absorption inhibitory action in living animals was tested under the following conditions.

After breeding 5-week old male wister rats (Clear Japan, Inc.) for more than one week, then 6 to 8-week old wister rats were used during the test. Without giving any food to the rats for 24 hours, sample of Embodiment 1 (at the rate of 0.5 g per kg of weight) was dissolved in distilled water, and carbohydrate (starch and sucrose: at the rate of 2 g per kg of weight) was dissolved in distilled water, then both were administered to the stomach sound.

To measure a variation of the blood glucose level after administering the samples to the rats, blood was taken from the vain of tails before the samples were administered, and at each stage of 30, 60, 120 and 180 min after the samples were administered. As a control group, blood was taken from the vain of the tails of the rats under the same conditions where the sample, the same amount of distilled water and carbohydrate (starch and sucrose at the rate of 2 g per kg of weight) were administered to the rats.

After centrifuging the blood taken from the rats, the blood glucose level of the supernatant was measured. For measuring the blood glucose level, a glucose measuring kit commercially available was used. ("Glucose B Test Wako" manufactured by Wako Pure Chemical Industries, Ltd., Japan) The results are shown in FIG. 1 and FIG. 2.

Figure 1:
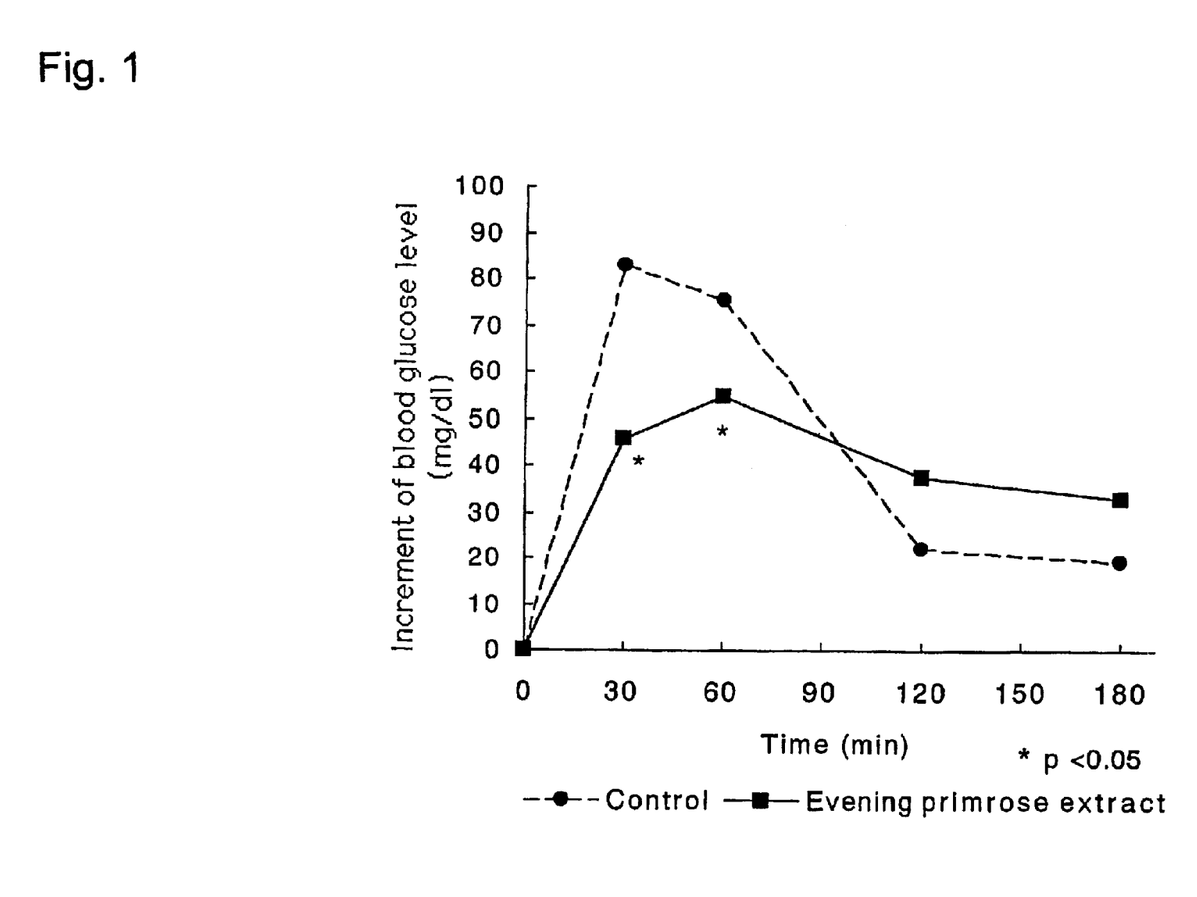
FIG. 1 on the attached sheet is a graph indicating a variation of blood glucose level of a normal rat after extracts of evening primrose seed and starch have been administered to the said rat.
Figure 2:
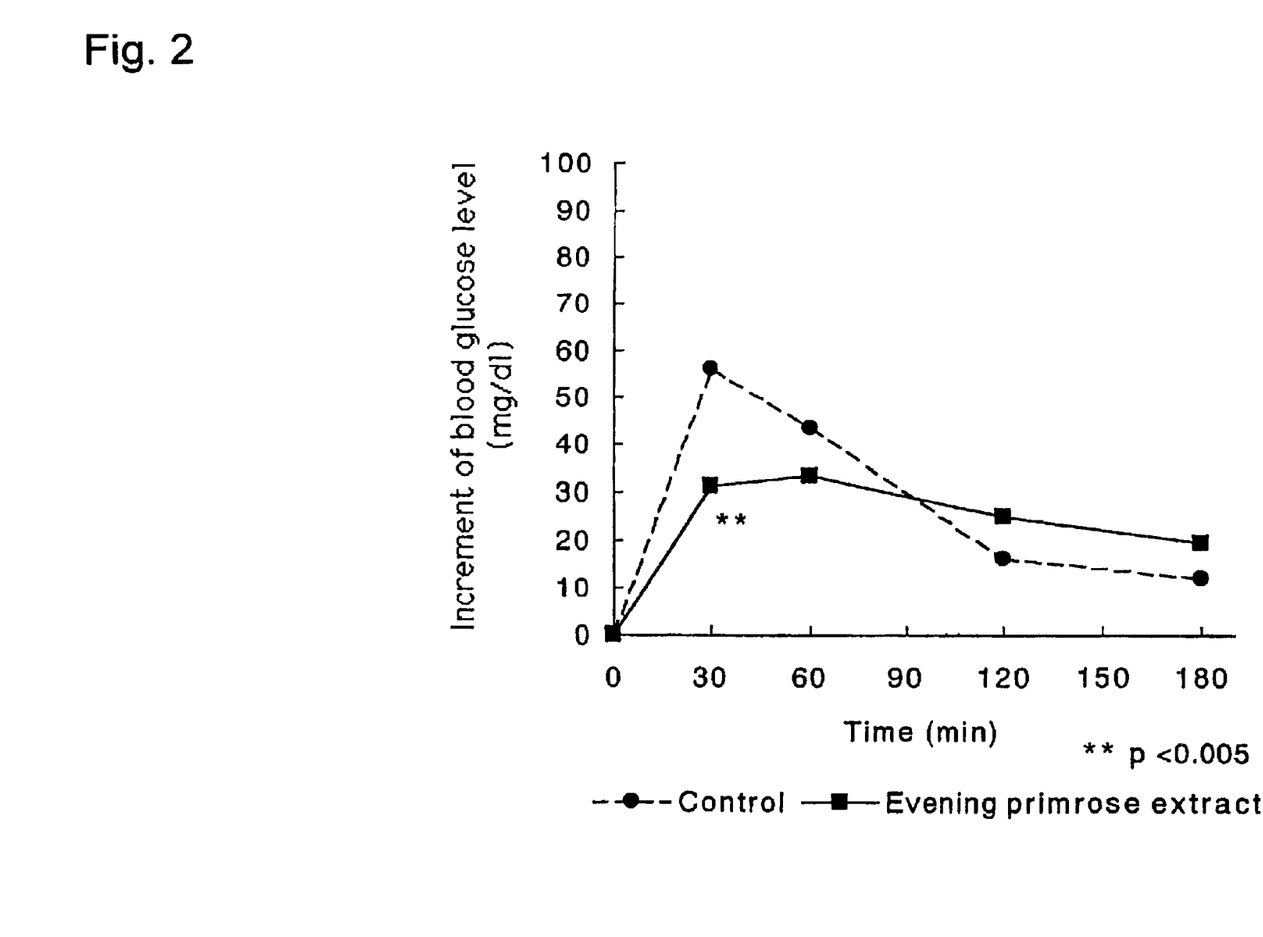
FIG. 2 on the attached sheet is a graph indicating a variation of blood glucose level of a normal rat after extracts of evening primrose and sucrose have been administered to the said rat.

As shown in FIG. 1 and FIG. 2, in a control group, the blood glucose level rapidly increased before 30 min passed, on the contrary, the blood glucose level of the rats of which the embodiment 1 (evening primrose seed extract) was administered slowly increased.

(Application to Food and Drink)

Application to food and drink which are effective for the prevention of diabetes mellitus and diet are as follows. "Evening primrose seed extract" shown below is powdered and dried ethanol extract of evening primrose seed obtained under the same conditions of the aforementioned embodiment 1.

| Composition 1: Chewing gums | |
|---|---|
| Sugar | 53.0 wt % |
| Gum base | 20.0 |
| Glucose | 10.0 |
| Starch syrup | 16.0 |
| Flavoring agent | 0.5 |
| Evening primrose seed extract | 0.5 |
| | 100.0 wt % |

| Composition 2: Gummy candies | |
|---|---|
| Reduced syrup | 40.0 wt % |
| Granulated sugar | 20.0 |
| Glucose | 20.0 |
| Gelatin | 4.7 |
| Water | 9.68 |
| Japanese apricot (Ume) juice | 4.0 |
| Japanese apricot (Ume) flavor | 0.6 |
| Coloring agent | 0.02 |
| Evening primrose seed extract | 1.0 |
| | 100.0 wt % |

| Composition 3: Candies | |
|---|---|
| Sugar | 50.0 wt % |
| Starch syrup | 33.0 |
| Water | 14.4 |
| Organic acid | 2.0 |
| Flavoring agent | 0.2 |
| Evening primrose seed extract | 0.4 |
| | 100.0 wt % |

| Composition 4: Soft capsule | |
|---|---|
| Rice germ oil | 87.0 wt % |
| Emulsifying agent | 12.0 |
| Evening primrose seed extract | 1.0 |
| | 100.0 wt % |

| Composition 5: Soft drink | |
|---|---|
| Fructose and glucose | 30.0 wt % |
| Emulsifying agent | 0.5 |
| Evening primrose seed extract | 0.05 |
| Flavoring agent | Minute amount |
| Distilled water | Rest |
| | 100.0 wt % |

| Composition 6: Tablets | |
|---|---|
| Lactose | 54.0 wt % |
| Crystallized cellulose | 30.0 |
| Starch degradation product | 10.0 |
| Glycerin fatty acid ester | 5.0 |
| Evening primrose seed extract | 1.0 |
| | 100.0 wt % |

| Composition 7: Tablet-shaped candies | |
|---|---|
| Sugar | 76.4 wt % |
| Glucose | 19.0 |
| Glycerin fatty acid ester | 0.2 |
| Evening primrose seed extract | 0.6 |
| Distilled water | 3.9 |
| | 100.0 wt % |

The structure of the extract obtained from the embodiment 1 and similar method contained ellagic acid, gallic acid, catechin, and pentagalloylglucose.

(Beginning of the Additional Part)

Analysis in regard to evening primrose seed extract in this invention is shown in chart 3 below.

CHART 3

| Sample | Gallic acid | Catechin | Ellagic acid | PGG*1 |
|---|---|---|---|---|
| Evening primrose extract Lot: R-006 | 2.7% | 1.6% | 0.5% | 2.3% |

*1: Pentagalloylglucose

Figure 3:
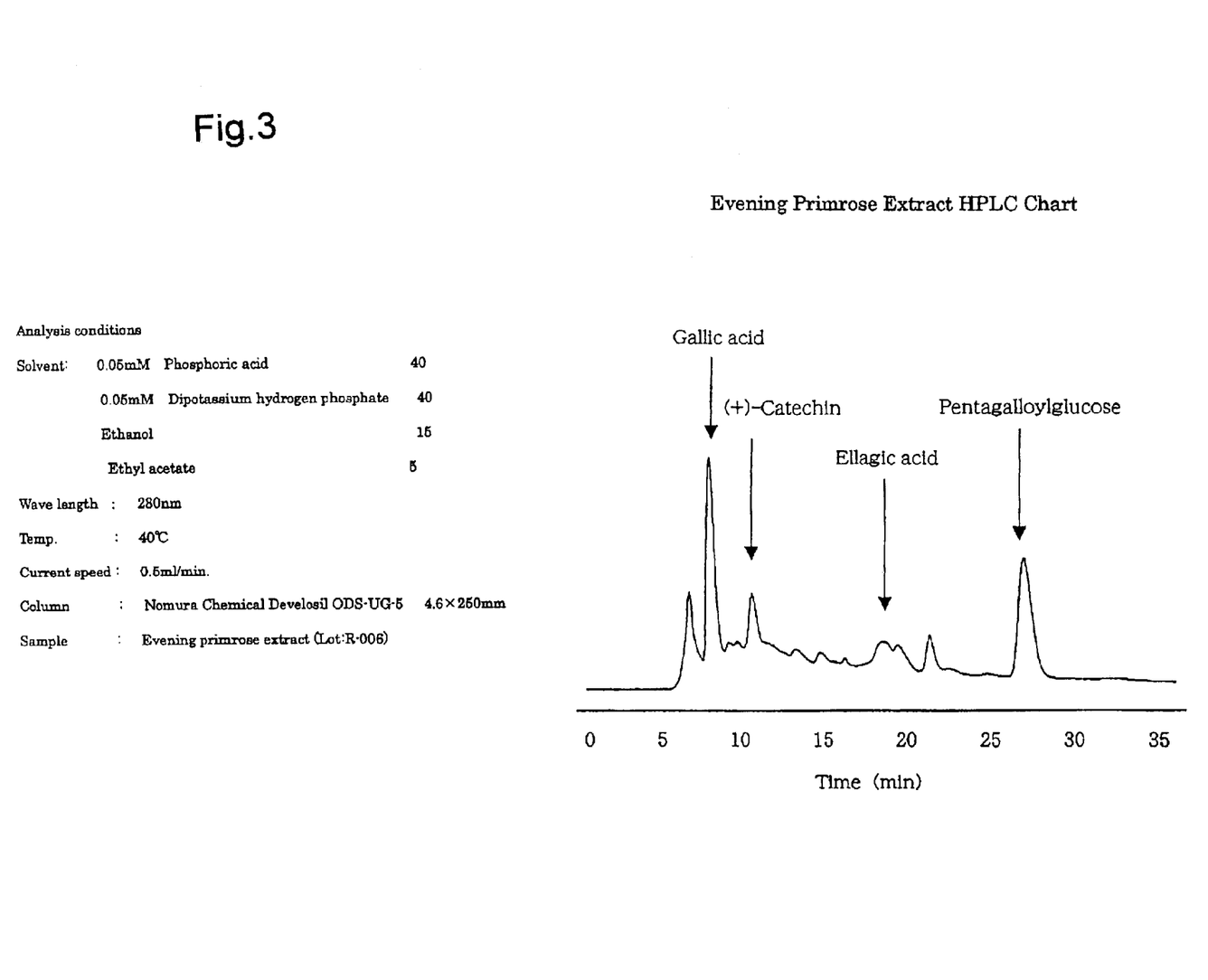
FIG. 3 on the attached sheet is an HPLC chart of the extract in this invention
Figure 4:
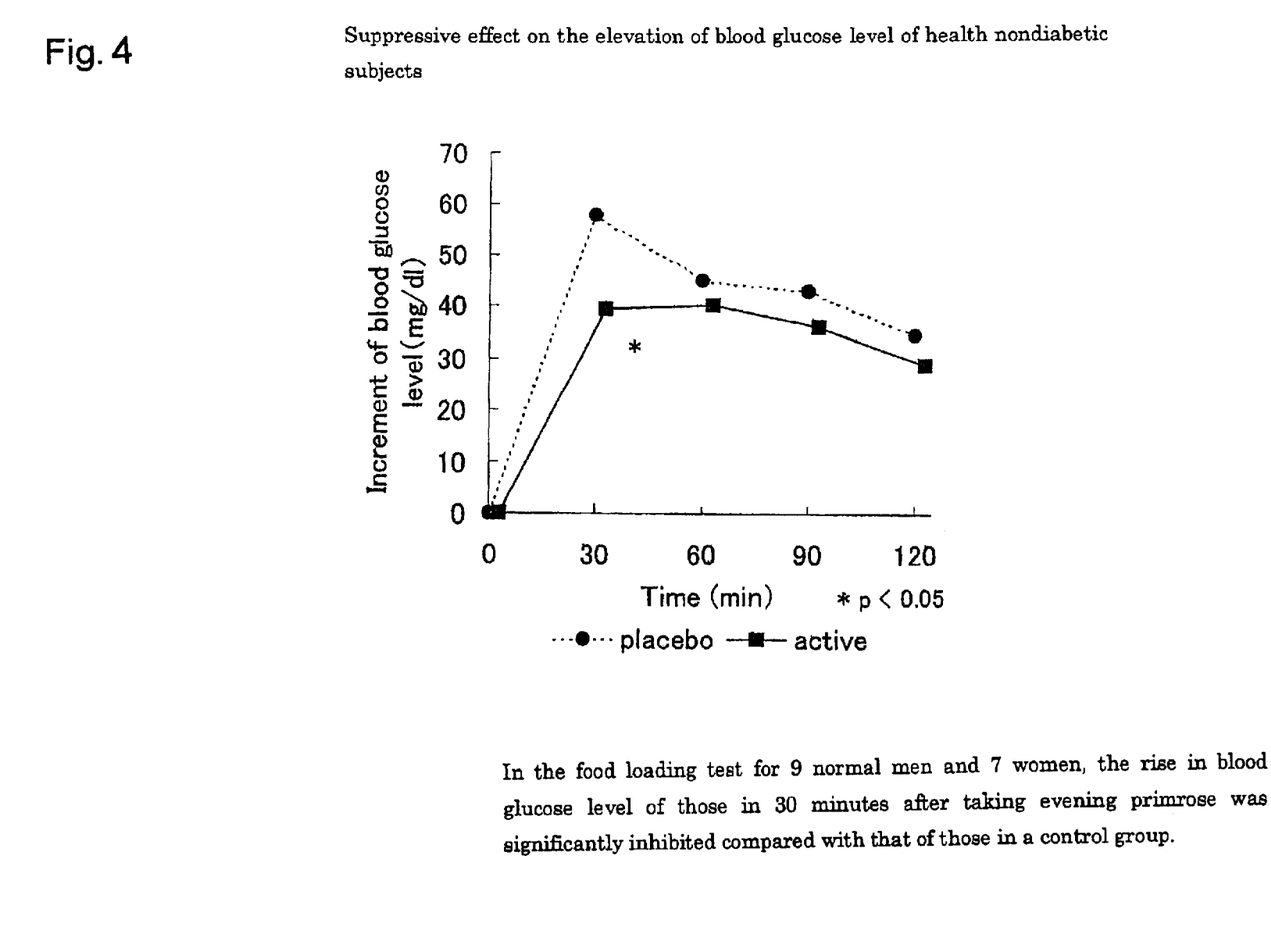
FIG. 4 on the attached sheet is a graph indicating a suppressive effect on the elevation of blood glucose level of the nondiabetic subject.
Figure 5:
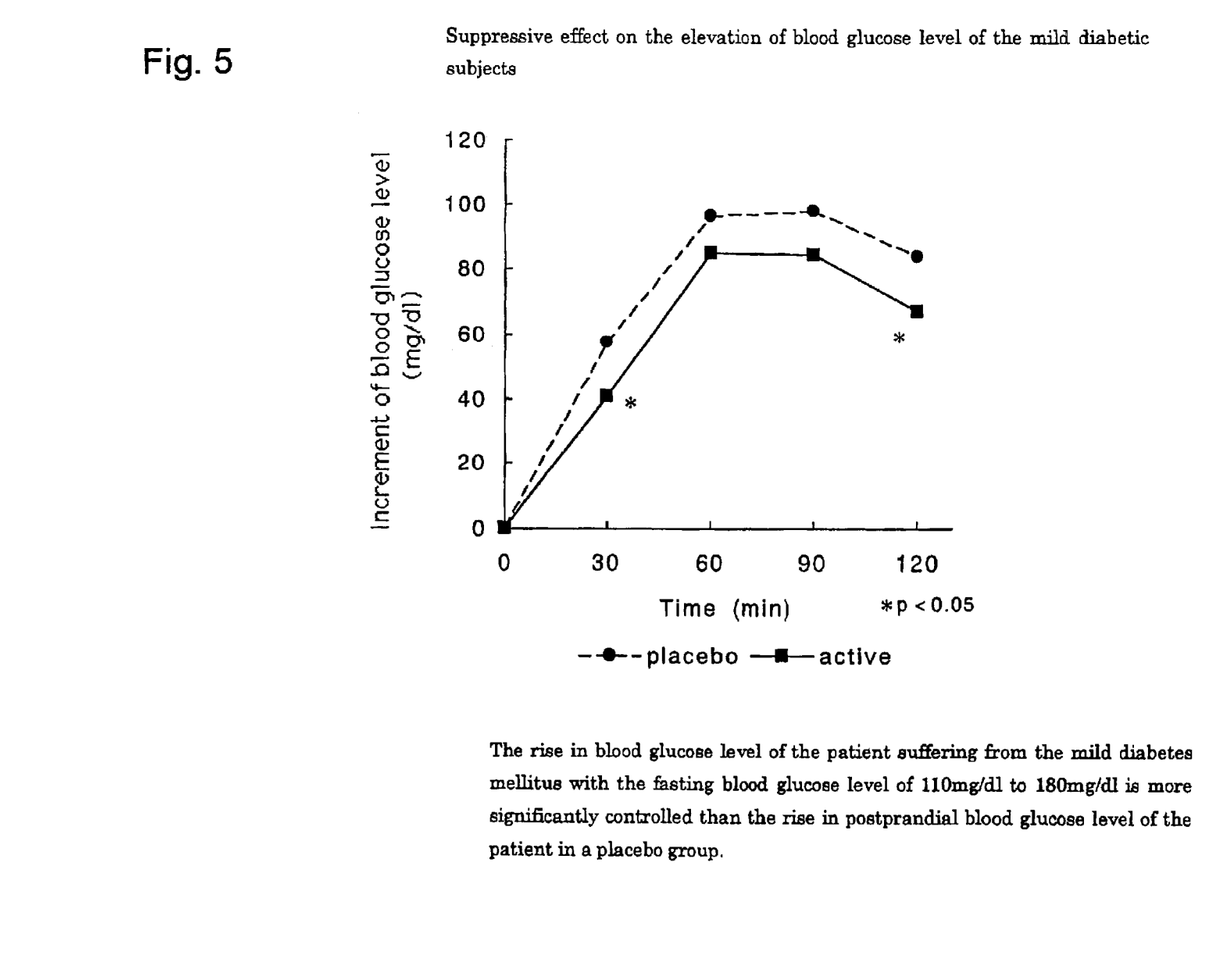
FIG. 5 on the attached sheet is a graph indicating a suppressive effect on the elevation of blood glucose level of the mild diabetic subjects.

Also, HPLC chart is shown in FIG. 3. Considering the above result, it is recognized that the extract obtained in this invention contains gallic acid, catechin, ellagic acid and pentagalloylglucose. It is still impossible to create a sample excluding the specific component from the evening primrose seed extract even by the present technology. Therefore, performance test should be still conducted by using a mixture of various components. After measuring the effectiveness to inhibit the after-meal elevated blood glucose level of 16 normal persons (female:male=7:9), the result in FIG. 4 shows that blood glucose level of subjects in 30 minutes after taking evening primrose is controlled. Also, the rise in blood glucose level of the patient suffering from the mild diabetes mellitus with the fasting blood glucose level of 110 mg/dl to 180 mg/dl is more significantly controlled than the rise in postprandial blood glucose level of the patient in a placebo group.

CHART 4

Change in the value of insulin when conducting the food loading test ($\mu$U/dl)

| | Before loading test | 30 min | 60 min | 90 min | 120 min |
|---|---|---|---|---|---|
| Control | 13.3 ± 15.0 | 28.4 ± 23.9 | 40.0 ± 31.1 | 43.6 ± 28.1 | 50.1 ± 30.0 |
| Evening primrose extract group | 12.7 ± 9.8 | 22.4 ± 14.5 | 35.8 ± 33.1 | 43.7 ± 35.9 | 43.7 ± 31.4 |

CHART 4-continued

Change in the value of insulin when conducting the food loading test ($\mu$U/dl)

|  | Before loading test | 30 min | 60 min | 90 min | 120 min |
|---|---|---|---|---|---|
| Significant difference between groups | n.s | n.s | n.s | n.s | n.s |

It is apparent that evening primrose comprises an effective function to control the rapid rise in blood glucose level after food loading. Since the rapid rise in blood glucose level is controlled, the rapid increase in insulin secretion becomes moderate. This indicates that evening primrose extract is effective to reduce the burden of insulin secretion of the patient suffering from insulin deficiency diabetes mellitus.
(End of the Additional Part)

INDUSTRIAL APPLICABILITY (Beginning of the Additional Part)

The amount of carbohydrate taken into the human body can be controlled by inhibiting the digestion of starch and saccharides, i.e., by inhibiting the activity of $\alpha$-amylase and $\alpha$-glucosidase which are saccharides degrading enzyme inherent in living body. The risk of type II diabetes mellitus can be especially controlled by a mechanism which keeps the postprandial blood glucose level low.

The said mechanism is significantly safer and harmless than the direct prevention to control the insulin secretion, and from the viewpoint of the preventive medicine in the latest mainstream of alternative medicine, it is considered to be inventive that the said mechanism can be applied to the function of the evening primrose leaf extract.

Also clinical investigation of the diabetes patient apparently shows that administration of evening primrose does not directly enhance the insulin secretion, and decrease in the blood glucose level of human and animals apparently indicates that evening primrose extract inhibit the absorption of the saccharides.
(End of the Additional Part)

As described above, absorption of saccharides can be effectively controlled in this invention.

Also this invention can provide the significant effectiveness to prevent and treat diabetes mellitus and obesity since the rise in blood glucose level by absorption of saccharides becomes moderate.

Furthermore, in this invention, effective component is extracted from evening primrose seed which is known as an ingredient of edible oil, therefore the said component is safe and has no side effect or the like.

What is claimed is:

1. A carbohydrate absorption inhibitor comprising an extract of a compressed and defatted caked of evening primrose seed, wherein oil is removed from an evening primrose seed by first comprising the seed into a cake for oil removal, and then using a solvent to remove remaining oil from the cake, and finally the cake treated with 70–85% (v/v) aqueous ethanol to produce the extract, the extract containing polyphenol-essential elements comprising ellagic acid, gallic acid, pentagalloylglucose and catechin.

2. The carbohydrate absorption inhibitor as described in claim 1 and characterized in that a fat-soluble organic solvent is used in when defatting the evening primrose seed.

3. A medicine comprising the carbohydrate absorption inhibitor as described in claim 1.

4. A food or drink comprising the carbohydrate the absorption inhibitor as described in claim 1.

5. A medicine comprising the carbohydrate absorption inhibitor as described in claim 2.

6. A food or drink comprising the carbohydrate absorption inhibitor as described in claim 2.

7. A method of making an extract from evening primrose seed wherein the seed is de-fatted and a solvent is used for extraction, the method comprising:

removing oil by an evening primrose seed by first compressing the seed into a cake;

using a solvent to remove remaining oil from the cake; and finally subjecting the cake to aqueous ethanol extraction, wherein 70% to 85% (v/v) aqueous ethanol solvent is used for extracting of a carbohydrate absorption inhibitor, the carbohydrate absorption inhibitor containing essential elements comprising ellagic acid, gallic acid, pentagalloylglucose and catechin.

* * * * *

UNITED STATES PATENT AND TRADEMARK OFFICE
CERTIFICATE OF CORRECTION

PATENT NO.    : 6,932,990 B2
DATED         : August 23, 2005
INVENTOR(S)   : Konishi et al.

It is certified that error appears in the above-identified patent and that said Letters Patent is hereby corrected as shown below:

Title page,
Item [75], Inventors, "Tsutomi Arimuba" should read -- Tsutomu Arimura --.

Signed and Sealed this

Twenty-seventh Day of December, 2005

JON W. DUDAS
*Director of the United States Patent and Trademark Office*